United States Patent
Bova et al.

[11] Patent Number: 5,954,647
[45] Date of Patent: *Sep. 21, 1999

[54] MARKER SYSTEM AND RELATED STEREOTACTIC PROCEDURE

[75] Inventors: Frank J. Bova; William A. Friedman, both of Gainesville, Fla.

[73] Assignee: University of Florida Research Foundation, Inc., Gainesville, Fla.

[*] Notice: This patent is subject to a terminal disclaimer.

[21] Appl. No.: 08/638,088

[22] Filed: Apr. 26, 1996

Related U.S. Application Data

[63] Continuation-in-part of application No. 08/388,024, Feb. 14, 1995, Pat. No. 5,588,430.

[51] Int. Cl.$^6$ .................................................. A61B 19/00
[52] U.S. Cl. .................... 600/407; 606/130; 378/205; 433/213; 433/75
[58] Field of Search ...................... 128/653.1, 653.2, 128/653.5, 664, 665, 898; 606/130; 378/62, 68, 204, 205, 207, 208; 600/1, 3, 7, 407, 410, 421, 473, 476; 433/68, 73, 75, 213, 29, 27

[56] References Cited

U.S. PATENT DOCUMENTS

| | | | |
|---|---|---|---|
| 4,228,799 | 10/1980 | Anichkov et al. | 128/303 B |
| 4,673,352 | 6/1987 | Hansen | 433/69 |
| 4,794,629 | 12/1988 | Pastyr et al. | 378/152 |
| 4,841,965 | 6/1989 | Jacobs | 128/303 B |
| 4,971,060 | 11/1990 | Schneider et al. | 128/653.1 |
| 5,005,578 | 4/1991 | Greer et al. | 128/653 A |
| 5,027,818 | 7/1991 | Bova et al. | 128/653 R |
| 5,037,374 | 8/1991 | Carol | 600/1 |
| 5,090,047 | 2/1992 | Angotti et al. | 378/170 |
| 5,165,106 | 11/1992 | Barthelmes et al. | 250/505.1 |
| 5,176,689 | 1/1993 | Hardy et al. | 606/130 |
| 5,189,687 | 2/1993 | Bova et al. | 378/65 |
| 5,197,476 | 3/1993 | Nowacki et al. | 128/660.03 |
| 5,205,289 | 4/1993 | Hardy et al. | 128/653.1 |
| 5,249,581 | 10/1993 | Horbal et al. | 128/664 |
| 5,250,019 | 10/1993 | McGinley | 600/1 |
| 5,269,305 | 12/1993 | Corol | 128/653.1 |
| 5,278,886 | 1/1994 | Kobiki et al. | 378/65 |
| 5,281,232 | 1/1994 | Hamilton et al. | 606/130 |
| 5,295,483 | 3/1994 | Nowacki et al. | 128/660.03 |
| 5,300,080 | 4/1994 | Clayman et al. | 606/130 |

(List continued on next page.)

OTHER PUBLICATIONS

Friedman et al, "Linear Accelerator Radiosurgery at the University of Florida," reprinted from Neurosurgery Clinics of North America, vol. 3, No. 1, pp. 141–166 (Jan. 1992).

*Primary Examiner*—Marvin M. Lateef
*Assistant Examiner*—Shawna J. Shaw
*Attorney, Agent, or Firm*—Kerkam, Stowell, Kondracki & Clarke; Dennis P. Clarke

[57] ABSTRACT

Repeat fixation for medical procedures is accomplished using a non-invasive locator, specifically a bite plate. The bite plate has at least three fiducial markers on it. The fiducial markers may be LEDs, radiopaque markers for angiography or computerized tomography (CT) imaging or magnetic resonance markers for magnetic resonance (MR) imaging. By detecting the position of the markers, the position of features within the patient (such as a brain tumor or other intracranial target to which radiation is to be applied) can be determined with great precision. Since the bite plate has been molded to uniquely fit to the patient's teeth, it may be removed after an initial imaging of the patient. The bite plate may then be re-attached one or more times to the teeth. An alternate embodiment uses a head ring or head holder such as a head mask system with the LEDs thereon. The head ring is useful for single fraction treatments. A comparison is made between the relative patient position and the position of a medical device and a desired relative positioning. One or more error signals are the result of the comparison and are used for display purposes such that a person may manually null or minimize the errors or as feedback control signals for automatic error correction.

20 Claims, 9 Drawing Sheets

U.S. PATENT DOCUMENTS

| | | | |
|---|---|---|---|
| 5,309,913 | 5/1994 | Kormos et al. | 128/653.1 |
| 5,370,117 | 12/1994 | McLaurin, Jr. | 128/653.1 |
| 5,380,336 | 1/1995 | Misko et al. . | |
| 5,383,454 | 1/1995 | Bucholz | 128/653.1 |
| 5,389,101 | 2/1995 | Heilbrun et al. . | |
| 5,397,329 | 3/1995 | Allen . | |
| 5,431,162 | 7/1995 | McArdle . | |
| 5,464,411 | 11/1995 | Schulte et al. | 606/130 |
| 5,513,240 | 4/1996 | Hausman et al. . | |
| 5,531,229 | 7/1996 | Dean et al. . | |
| 5,588,430 | 12/1996 | Bova et al. . | |
| 5,622,187 | 4/1997 | Carol | 128/897 |
| 5,630,422 | 5/1997 | Zanakis | 128/664 |

MARKER SYSTEM AND RELATED STEREOTACTIC PROCEDURE

CROSS-REFERENCE TO RELATED APPLICATION

This application is a continuation-in-part of U.S. patent application Ser. No. 08/388,024 filed Feb. 14, 1995 now U.S. Pat. No. 5,588,430 in the names of Frank J. Bova, Ph.D. and William A. Friedman, the inventors herein. That application, which is assigned to the assignee of the present application, is hereby incorporated by reference.

BACKGROUND OF THE INVENTION

The present invention relates to a device, system and method for stereotactic medical procedures. More specifically, it provides for accurate positioning (fixation) of a patient or part of a patient for carrying out medical procedures, singly or multiple times.

The discussion below will initially focus on medical procedures where the procedure is performed multiple times on the same patient.

Various medical procedures involve repeated treatments at different times. For example, application of radiation is sometimes used for treating brain tumors or other conditions. Although a single application of radiation may sometimes be used, under many circumstances there are sound medical reasons to use repeated application of radiation at different times.

The treatment of a radiation therapy patient can be broken down into four stages. These are (1) diagnostic evaluation, (2) treatment planning, (3) simulation and (4) treatment. Our repeat fixation device is applicable to the latter three phases of the treatment process. In the first stage of diagnostic evaluation the physician decides which tissues are at risk of disease and should be targeted. The patient may undergo many diagnostic tests including angiography, computerized tomography (CT) and magnetic resonance (MR) imaging. After the physician is satisfied that they have identified the tissues at risk, the patient then undergoes a process known as treatment simulation. This process involves obtaining a set of images such as plane films, digital images, CT, MRI, and ultrasound images. These radiographs allow the physician to select a specific path for each radiation beam which only includes the tissues at risk and excludes normal tissues. Because the tissues the physician has targeted are often radiographically transparent the physician routinely relies upon radiographic landmarks to infer the proper beam alignment. These same landmarks are subsequently imaged on similar radiographs taken with the therapeutic x-ray beam prior to administering the radiation treatment. These pre-treatment radiographs, which are known as therapy portal films, allow the physician to judge the appropriate alignment of the treatment beam and the patients anatomy. The frequency at which these portal films are repeated is dependent upon the complexity of the patient setup and the proximity of the beam to critical structures (such as a patient's optic nerve).

A routine course of radiation therapy may span anywhere from 10 to 64 fractions over a period of two to six weeks. The number of treatments dependent upon the specifics of the particular disease. For each fraction the patient must be repositioned at the teletherapy unit and aligned relative to the radiation beam.

There exists a clinical situation in which the target tissues cannot be adequately localized by their proximity to radiographically opaque structures as required by the above simulation procedure. Arteriovenous malformations, acoustic neurinomas and other small intracranial targets are examples of such clinical entities. To enable the identification, and subsequent treatment of such targets, a new and very powerful technique known as radiosurgery has been developed. (Radiosurgery is usually considered to be a single fraction radiotherapy treatment, meaning a single treatment, although it may also be more broadly interpreted. Multiple radiotherapy treatments are often called high precision radiotherapy or fractioned stereotactic radiotherapy.) This technique allows small intracranial targets to be identified and treated to a very high degree of precision.

The radiosurgical technique uses stereotactic principles for targeting, localization and treatment. The procedure begins with a stereotactic reference system being fixed to the patient's skull. This reference system remains fixed relative to all intracranial points throughout the entire radiosurgical procedure. All diagnostic exams, such as angiography, CT and MR scanning include a set of fiducial markers which allow all points within the image to be localized relative to the stereotactic reference frame.

Once the target tissues have been identified the path of radiation beams can be mathematically computed. The computer algorithms, which support this procedure, allow the clinician to evaluate the amount of dose which would be deposited within the patient if the simulated beams were actually x-ray beams were applied along the proposed paths. In an attempt to arrive at a treatment plan which adequately confines the radiation dose to the target tissues while limiting the dose to all normal tissues the beams of radiation are modified, eliminated or new beams added to the plan. Once a plan with an acceptable dose distribution has been arrived at the information on beam trajectory is transferred to the radiotherapy treatment unit. A single fraction of radiation is then given to the patient and the stereotactic frame is removed. The entire length of the procedure, from frame application through treatment, usually spans 6 to 8 hours.

The present inventors' prior U.S. patents listed below, assigned to the assignee of the present application and hereby incorporated by reference disclose techniques for providing stereotactic radiosurgery with a high degree of precision:

| U.S. Pat. No. | Issue Date | Title |
| --- | --- | --- |
| 5,027,818 | July 2, 1991 | DOSIMETRIC TECHNIQUE FOR STEREOTACTIC RADIOSURGERY |
| 5,189,687 | February 23, 1993 | APPARATUS FOR STEREOTACTIC RADIOSURGERY |

The techniques of the inventors' above patents allow the patient to be precisely positioned relative to radiation beams of stereotactic radiosurgery to within 0.2 mm plus or minus 0.1 mm. Although this works very well for single fraction therapy, there exist clinical settings where fractionating the total dose, i.e. dividing the dose into many small fractions, would yield additional therapeutic advantage. In the radiotherapy procedure, once the reference frame has been removed from the patient the relationship between intracranial target points and the reference system is lost. Because the above procedure would require the reference frame to remain fixed to the patient's skull through the entire course of treatment, which may last several weeks, this approach is considered inappropriate for fractionated therapy. Alternately, each fractional treatment would require a laborious and time-consuming procedure to re-determine patient position for second and subsequent treatments.

There exist several different techniques for non-invasive repeat fixation. These methods can be broken down into three basic categories. These are bite plate systems, contour realignment systems and mask systems. All of these systems have design flaws which can lead to unacceptable, and undetectable, positional errors.

The mask techniques have been used in radiation therapy for over three decades. In these systems a custom mask, which snugly fits either the face or the entire head, is fabricated. For high precision radiotherapy the mask is then attached to a stereotactic reference frame, similar to the frame used for any stereotactic procedure. Prior to each diagnostic exam the patient is placed into the mask/frame system and normal stereotactic fiducial systems are used for image registration.

Mask immobilization and repositioning systems have been used extensively in radiation therapy. From multiple reports in the literature mask systems appear to have a repeat fixation tolerance no better than 3 to 5 mm. It is our opinion that this level of accuracy is unacceptable for fractionated radiotherapy.

Bite plate systems have also been used in radiotherapy for several decades. This technique requires the fabrication of a customized bite plate. The plate fits snugly onto the patient's teeth. As with the mask/frame systems, the bite plate is fixed to a stereotactic reference frame which then accepts the routine set of fiducial markers for both plane film radiography, CT and MR scanning. The primary disadvantage of this system is that the bite plate is used for both localization and patient fixation. The bite plate not only provides the reference for stereotactic localization, but it also is the mechanism which is used to move the patient into position. Moving the patient by use of the bite plate produces torque on the bite plate-teeth interface. An analysis of this approach reveals that very small movements in the bite plate position, relative to the patient's teeth, can result in large translations and rotations of the intracranial targets. Since no method of alignment verification has ever been developed, these errors go undetected.

An alternate system for patient positioning uses the patient's own anatomical contours as the stereotactic reference system. In this approach a CT or MR scan is taken and a three dimensional reconstruction of the patient's surface is obtained. These contours act as the reference system for stereotactic localization.

The usual diagnostic exams are carried out and the treatment is then planned using the same stereotactic principles used in routine radiotherapy. The target is identified and the patient's surface contour coordinates are measured relative to the isocenter. The patient is placed at the teletherapy treatment unit and the surface contours are again obtained through the use of surface digitization. A set of algorithms then calculate the translations as well rotations required to reposition the patient's target over the teletherapy units isocenter. The accuracy of such systems under clinical test conditions have been shown to be approximately two to three mm.

When performing fractionated radiotherapy, accuracy in applying the radiation is very important. Some tumors or other conditions require that the radiation be concentrated in relatively small volumes. Misalignment of the radiation beam may cause an insufficient amount of radiation to be applied to the tumor or other target. Further, such misalignment may increase the likelihood and/or degree of damage to healthy tissue adjacent the tumor or other target.

Fractionated radiotherapy may be imprecise if the tumor or other target cannot be localized with a sufficient degree of accuracy. However, this need for proper localization is the same need which one has when performing single dose radiotherapy and this need is addressed by the present inventors' incorporated by reference patents. The additional factor in fractionated radiotherapy is the need to easily and accurately repeat a position of the patient. If the position of the patient was accurate relative to the first treatment, the repositioning should normally cause the patient to assume the exact same position (relative to the treatment mechanism) for the second and subsequent treatments. However, if the second or other subsequent treatment is performed with the patient only slightly moved from the first treatment position, this will introduce inaccuracies. The repeat fixation techniques discussed above have the indicated disadvantages.

More generally, the need for repeat fixation of a patient or portion of a patient exists outside of radiotherapy. In the general case, one wishes to perform a first medical procedure on a patient with a precise localization of portions of the patient, and, at some later time, perform a second medical procedure on the patient with a precise localization of portions of the patient. One can repeat laborious and time-consuming localization steps for the second medical procedure, but this increases medical costs and complexity. As used herein, a medical procedure is a procedure for diagnostic and/or remedial purposes.

In some situations, a single medical treatment without a need for repeat fixation is the desired course of treatment. However, a high degree of accuracy in positioning may still be required. The mechanical arrangements and the associated techniques of the present inventors' last mentioned above two incorporated by reference patents can provide a high degree of accuracy in positioning of the patient relative to the medical apparatus.

In such single medical treatment situations, the patient may require immobilization as well as localization. (Localization as used herein is accurate placement of a patient relative to a medical apparatus.)

The arrangements and the associated techniques of the present inventors' last mentioned above two incorporated by reference patents do provide a high degree of accuracy in positioning of the patient relative to the medical apparatus by compensating for the mechanical imprecisions in the joints and connections of various mechanical elements in the radiation head. However, imprecision which results from minor deviations in the interface between the patient and the head ring or other immobilization device may still limit the accuracy. The bite plate arrangement disclosed and claimed in the incorporated by reference Ser. No. 08/388,024 parent application can help to overcome this problem. However, other arrangements which can provide localization without using a bite plate would be useful.

OBJECTS AND SUMMARY OF THE INVENTION

Accordingly, it is a primary object of the present invention to provide a new and improved method and system for localization (i.e., proper relative positioning of a patient and a medical apparatus or system) in performing medical procedures.

A more specific object of the present invention is to provide precise and easy localization of a patient on which a medical procedure is to be performed.

Another object is to provide for highly precise non-invasive repeat fixation for repeating medical procedures.

A further object of the present invention is to provide repeat fixation in which a locator is mechanically independent from any structures used for positioning the patient. That is, any structure used to position the patient does not move the locator except by way of the patient.

Yet another object of the present invention is to provide repeat fixation for stereotactic radiotherapy.

A further object of the present invention is to provide repeat fixation which allows relatively fast re-localization of a patient after an initial localization.

Yet another object of the present invention is to provide repeat fixation which minimizes or avoids the disadvantages of prior techniques discussed above.

A further object of the present invention is to provide an accurate localization for a one treatment medical procedure where the relative position of the patient and a medical apparatus or system may be easily adjusted to achieve a desired relative position of the patient and a medical apparatus or system.

A further object of the present invention is to provide an accurate localization for a one treatment medical procedure where the relative position of the patient and a medical apparatus or system may be automatically adjusted to achieve a desired relative position of the patient and a medical apparatus or system.

The above and other features of the present invention which will be more readily understood when the following detailed description is considered in conjunction with the accompanying drawings are realized by a medical method including the steps, not necessarily in order, of: positioning a patient for a first medical procedure; and attaching a mechanically free locator to a patient, the locator having at least 3 LEDs (light emitting diode) thereon and being in registry with a portion of the patient. As used herein, a mechanically free locator is one which is used for localization without being rigidly fixed to a structure other than possibly a portion of a patient. LEDs are used a first time to get precise positioning information relative to at least part of the patient.

A first medical procedure is performed on the patient. After the first medical procedure, the locator is removed from the patient. At a later time, the locator is re-attached to the patient, the locator again being in registry with the portion of the patient and having an identical orientation relative to the portion of the patient as when the locator was previously attached. After the re-attaching step, the LEDS are used a second time to get precise positioning information relative to the at least part of the patient. After the re-attaching step, a second medical procedure is performed on the patient.

Preferably, the attaching and re-attaching of the locator is non-invasive. As used herein, non-invasive shall mean that no holes need to be created in a patient and no patient tissue needs to be removed in order to attach and re-attach the locator.

More specifically, the locator is a bite plate with an external portion connected thereto, and the LEDs are on the external portion. The attaching includes using a mold of dental impression material to bring the bite plate in registry with teeth of the patient, and wherein the re-attaching uses the mold to bring the bite plate in registry with teeth of the patient with an identical orientation relative to the teeth as when the bite plate was previously attached.

In one technique of the invention, the first medical procedure is an imaging of at least a portion of the patient and the second medical procedure is a remedial procedure treating at least one problem precisely localized in the first medical procedure. The second medical procedure may use a probe inserted in the patient for treatment of the patient or the second medical procedure includes radiotherapy.

In another aspect of the invention, both the first and second medical procedures include radiotherapy.

The using of the LEDs the first and second times utilizes a sensing subsystem for sensing the positions of the LEDs. Before performing the second medical procedure, the patient is positioned using a positioner independent of the locator to secure at least the portion of the patient in a desired position.

The present invention may alternately be described as a system for medical procedures, the system including a locator attachable to a patient, having at least 3 LEDs thereon, and having a registration portion for registration with a portion of a patient's body. The registration portion allows removal of the locator from the patient and re-attachment to the patient with an identical orientation relative to the portion of the patient as when the locator was previously attached. The locator is mechanically free such that a patient is positionable without applying forces to the locator during patient positioning. The system has a positioner independent of the locator and operable to secure at least the portion of the patient in a desired position. A sensing subsystem is operable for sensing the positions of the LEDs when the patient is in the desired position. The locator is non-invasive. The locator is more specifically a bite plate with an external portion connected thereto, and the LEDs are on the external portion, and the bite plate has dental impression material for fabrication of a mold to bring the bite plate in registry with teeth of the patient, and the mold is operable to bring the bite plate in registry with teeth of the patient with an identical orientation relative to the teeth as when the bite plate was previously attached.

The system further includes a radiotherapy apparatus for applying radiation treatment to a patient, the positioner and sensing subsystem allowing proper positioning of the patient for applying radiation treatment. The system further includes an imaging subsystem for imaging the patient.

The present invention may further be described as a medical method comprising the steps, not necessarily in order, of: positioning a patient for a first medical procedure; attaching a locator to a patient, the locator having at least 3 fiducial markers thereon and being in registry with a portion of the patient; using fiducial markers a first time to get precise positioning information relative to at least part of the patient; and performing a first medical procedure on the patient. After the first medical procedure, the locator is removed from the patient. At a later time after the removal of the locator, the locator is re-attached to the patient, the locator again being in registry with the portion of the patient and having an identical orientation relative to the portion of the patient as when the locator was previously attached. After the re-attaching step, fiducial markers are used a second time to get precise positioning information relative to at least part of the patient. After the re-attaching step, a second medical procedure is performed on the patient. The locator is a bite plate with an external portion connected thereto, and the fiducial markers are on the external portion, and wherein the attaching includes using a mold of dental impression material to bring the bite plate in registry with teeth of the patient. The re-attaching uses the mold to bring the bite plate in registry with teeth of the patient with an identical orientation relative to the teeth as when the bite plate was previously attached.

In one technique, the first medical procedure is an imaging of at least a portion of the patient and the second medical procedure is a remedial procedure treating at least one problem precisely localized in the first medical procedure. The second medical procedure uses a probe inserted in the patient for treatment of the patient or the second medical procedure includes radiotherapy.

In another technique of the invention, both the first and second medical procedures include radiotherapy.

In a specific aspect of the invention, the fiducial markers used the first time are objects other than LEDs and the fiducial markers used the second time are LEDs put on the external portion at locations of the objects.

In an alternate specific aspect of the invention, the fiducial markers used the first and second times are LEDs and the using of the fiducial markers the first and second times utilizes a sensing subsystem for sensing the positions of the LEDs. Before performing each of the first and second medical procedures, the patient is positioned using a positioner independent of the locator to secure at least the portion of the patient in a desired position.

The present invention may alternately be described as a system for medical procedures, the system including a locator attachable to a patient, having at least 3 fiducial markers thereon, and having a registration portion for registration with a portion of a patient's body, the registration portion allowing removal of the locator from the patient and re-attachment to the patient with an identical orientation relative to the portion of the patient as when the locator was previously attached, the locator being mechanically free such that a patient is positionable without applying forces to the locator during patient positioning. A positioner is independent of the locator and operable to secure at least the portion of the patient in a desired position. A sensing subsystem senses the positions of the fiducial markers when the patient is in the desired position. In a specific aspect of the invention, the locator is a bite plate with an external portion connected thereto, the fiducial markers are on the external portion, and the bite plate has a mold to bring the bite plate in registry with teeth of the patient, and the mold is operable to bring the bite plate in registry with teeth of the patient with an identical orientation relative to the teeth as when the bite plate was previously attached.

The system may further include a radiotherapy apparatus for applying radiation treatment to a patient, the positioner and sensing subsystem allowing proper positioning of the patient for applying radiation treatment. A radiotherapy apparatus configured for radiosurgery, a standard linear accelerator, a radiosurgery apparatus as described in the above prior patents, and any other device for applying therapeutic radiation would be considered a radiotherapy apparatus as the term is used herein.

The fiducial markers includes three LEDs which uniquely define a plane.

The present invention may alternately be described as a system for medical procedures including;
a locator attachable to a patient, having at
least 3 fiducial markers thereon;
a medical device for performing a medical procedure on a patient;
a sensing subsystem for sensing the positions of the fiducial markers when the patient is in
a position for performing the medical procedure using the medical device;
a first comparison means for comparing positioning information (i.e., as used herein positioning information is a broad term including position information and orientation information) of the patient and positioning information relative to the medical device and supplying actual offset information; and
a second comparison means for comparing the actual offset information with desired offset information and generating an error signal based thereon.

The first and second comparison means may be differential amplifiers or other circuit elements or may be one or more computer programs performing the comparisons.

In one embodiment, the locator has a registration portion for registration with a portion of a patient's body, the registration portion allowing removal of the locator from the patient and re-attachment to the patient with an identical orientation relative to the portion of the patient as when the locator was previously attached, the locator being mechanically free such that a patient is positionable without applying forces to the locator during patient positioning; and
wherein the locator is a bite plate with an external portion connected thereto, and the fiducial markers are on the external portion, and the bite plate has a mold to bring the bite plate in registry with teeth of the patient, and the mold is operable to bring the bite plate in registry with teeth of the patient with an identical orientation relative to the teeth as when the bite plate was previously attached.

In another embodiment the locator is selected from the group consisting of: a head ring secured to a support and a head holder secured to a support.

Preferably, the locator is a head ring and has a member secured thereto, and wherein the three fiducial markers are mounted to the member so as to uniquely define a plane (meaning that the three markers are not in a straight line).

The invention may alternately be described as a system for medical procedures, the system including:
a head holding device attachable to a patient's head and having at least 3 LEDs thereon, the 3 LEDs uniquely defining a plane, the head holding device serving as a localizer and immobilizer for the patient, the 3 LEDs operable to allow the sensing of patient position information for performance of a stereotactic procedure on the patient's head; and
wherein the head holder device is selected from the group consisting of: a head ring secured to a support and a head holder secured to a support.

The invention may alternately be described as a method for performing a medical procedure including the steps of, not necessarily in order:
attaching a locator to a patient, the locator having at least 3 fiducial markers thereon;
placing the patient adjacent a medical device operable for performing a medical procedure on a patient;
sensing the positions of the fiducial markers when the patient is in a position for performing the medical procedure using the medical device; and
generating error signals dependent on differences between actual patient position information relative to the medical device and a desired patient position relative to the medical device.

The method further includes the step of adjusting the relative positioning of the patient and the medical device to null or minimize the error signals. This step may be accomplished manually by a person or through a feedback control arrangement.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
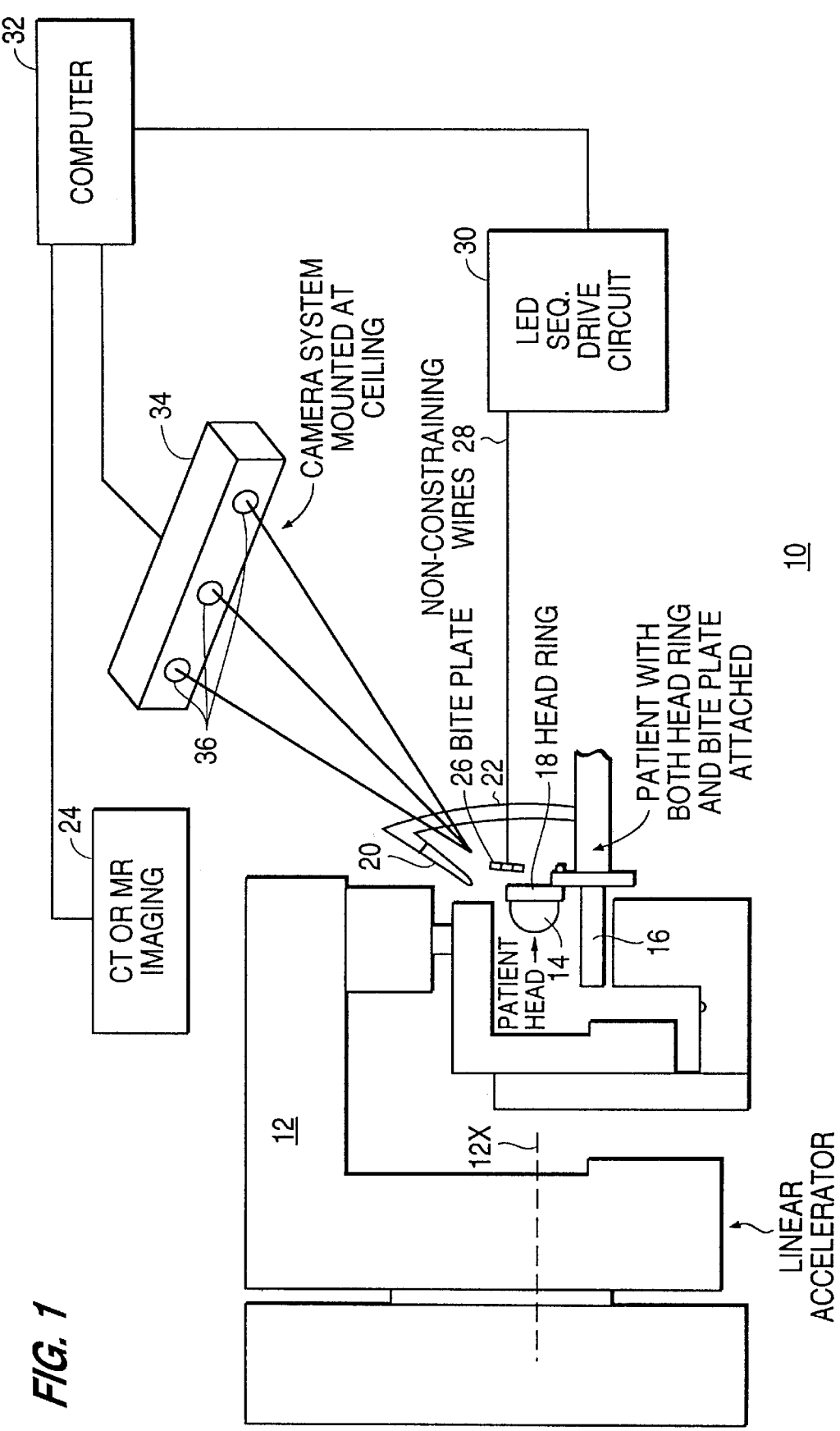
FIG. 1 is a simplified diagram of the system of the present invention.

The system 10 of the present invention is shown in FIG. 1 as having a linear accelerator 12 for performing stereotactic radiotherapy on a patient's head 14 which is on a surgical table 16 (shown only partially) and secured thereto by way of a head ring 18. The details of the accelerator 12 and table 16 are not a necessary part of the present invention and need not be discussed. Moreover, these would be constructed and operable in the manner discussed with respect to the structures and techniques of the above incorporated by reference U.S. Patents of the inventors, this allowing the precision application of radiotherapy to the patient.

As an alternative or additionally to the accelerator 12, a probe 20 (constructed in known fashion) for stereotactic surgery may be mounted to anchor 22 secured to the table 16 as shown or to a wall or other structure such as a linear accelerator, CT, MR, or any other reference required (not shown). The probe 20, which is a scalpel, laser, or other surgical apparatus, may alternately have LEDs thereon for sensing the exact position and direction (orientation) of the probe in space using known techniques such that the probe need not be attached to anything) A further alternative or additional feature may be an imaging system such as computerized tomography (CT) or magnetic resonance (MR) system 24. One or more of the accelerator 12, probe 20, and imaging system 24 are used to perform medical procedures on the patient.

The present invention provides for repeated fixation of a locator in registry with (i.e., uniquely positioned relative to) a portion of a patient. Before discussing details of how this is accomplished, it will generally be noted that the locator is used to provide a frame of reference for performing a first medical procedure and the locator is then removed. The locator is then re-attached to the patient such that a second medical procedure could be performed. The medical procedures may be any diagnostic and/or treatment procedures. However, the discussion which follows will emphasize use of the technique for fractionated stereotactic radiotherapy.

The present system uses a bite plate 26 connected by non-constraining (i.e., they are loose and do not significantly pull on the bite plate) wires 28 to an LED sequential drive circuit 30. (In lieu of the wires, a wireless arrangement, not shown, could be used to strobe the LEDs or a drive circuit could be on the bite plate itself.) Circuit 30 is also connected to a computer 32. The computer is connected to the imaging system 24 and a camera system 34. The camera system 34, which serves as a sensing subsystem, may be of a known type having several cameras 36 as part thereof in order to locate the bite plate 26 by way of several LEDs (not shown in FIG. 1) thereon. The camera system 34 and technique for strobing the LEDs (sequentially lighting them one at a time) may be that disclosed in U.S. Pat. No. 5,198,877, issued to Schulz on Mar. 30, 1993, assigned on its face to PixSys, Inc, and hereby incorporated by reference. Such a camera system is commercially available from PixSys, Inc.

Figure 2:
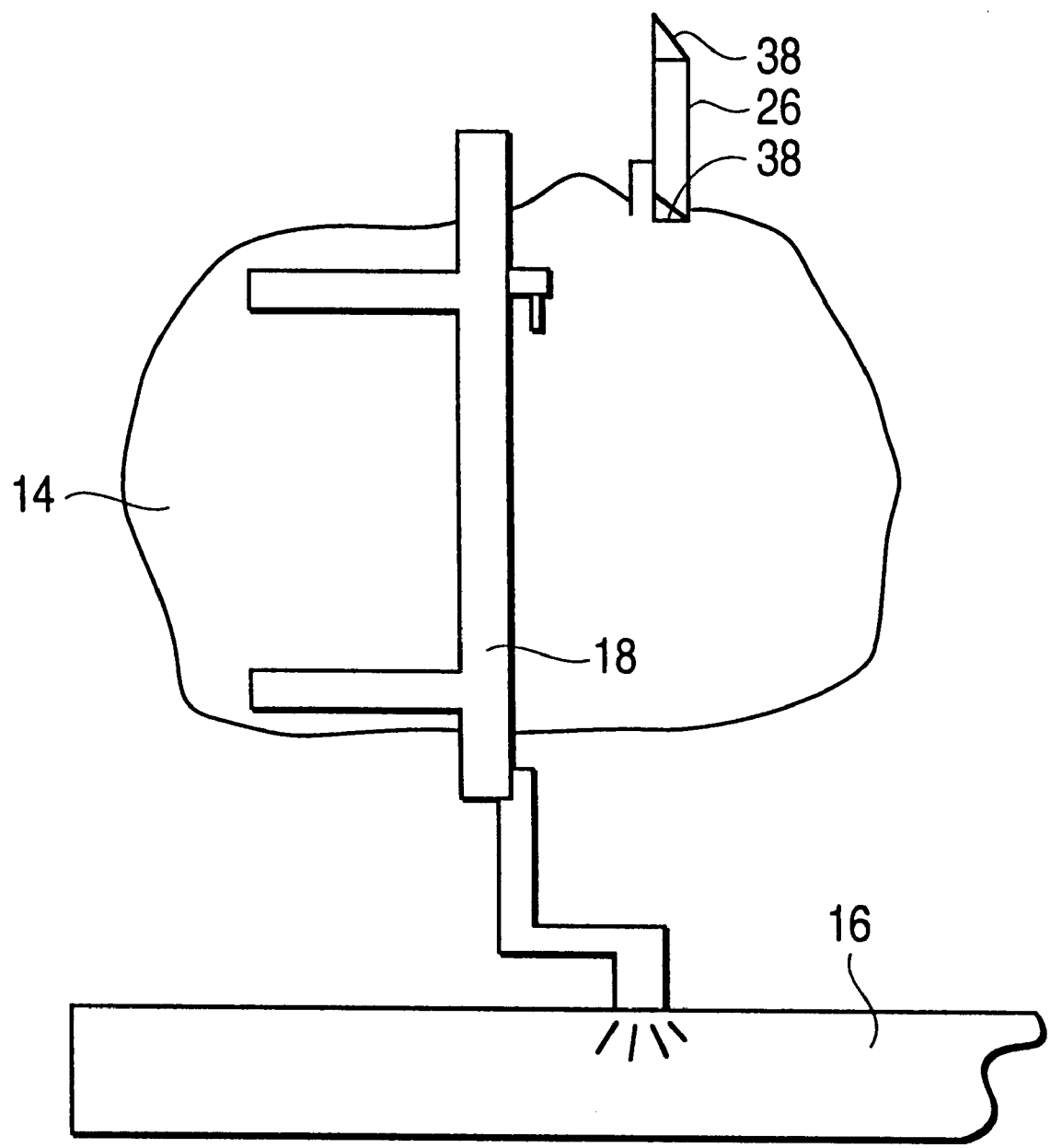
FIG. 2 is an enlarged side view of a patient's head with portions of the present invention attached thereto.

With reference now to FIG. 2, the patient's head 14 is restrained and can be positioned by use of a head ring 18, which ring would then be fixed in place using techniques discussed in the present inventors' incorporated by reference patents. The head ring 18 may be of any type used or developed to constrain the head.

The bite plate 26 is a type of locator and has at least three LEDs 38 (only two visible in FIG. 2) thereon. The three LEDs are not in a line and therefore uniquely define a plane. Most advantageously, the bite plate 26 is mechanically free such that a patient is positionable without applying forces to the locator during patient positioning. The bite plate 26 is more specifically independent any structures (such as ring 18) used for positioning the patient (such structures being called positioning structures). That is, any structure used to position the patient does not move the bite plate 26 except by way of the patient. In that fashion, no forces or torques are applied to the bite plate 26 which might cause it to slightly change its position relative to the patient.

Figure 4:
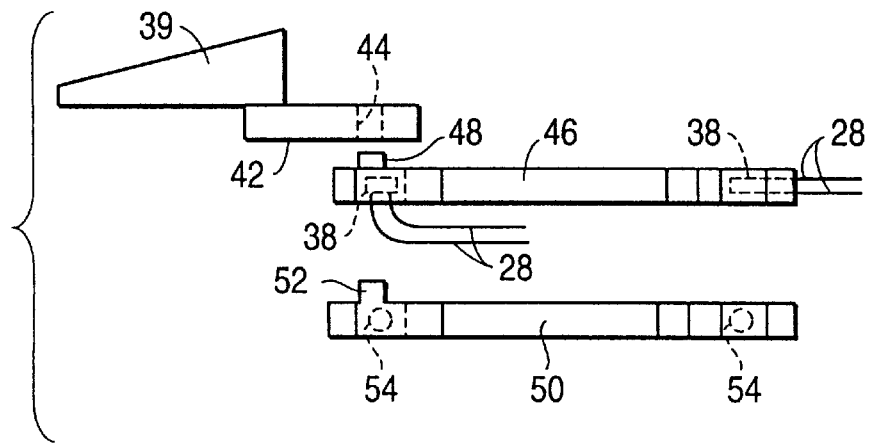
FIG. 4 is an exploded view of the locator of FIG. 3.
Figure 3:
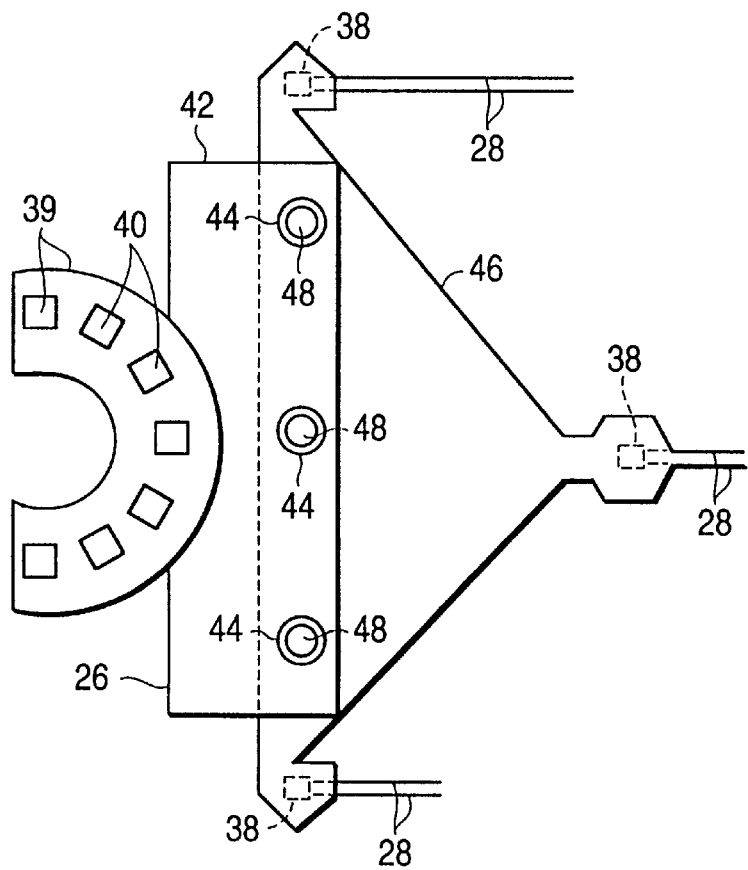
FIG. 3 is a detailed view of locator according to the present invention.

With reference to FIGS. 3 and 4, the bite plate 26 has a plastic mouth portion 39 having tooth imprints 40 (only a few shown for ease of illustration) previously formed of dental mold material on mouth portion 38 in known fashion. A mount plate 42 is integral with or fixed to mouth portion 39. Three holes 44 are disposed within the mount plate 42 and allow it to removably receive a marker plate 46 having three posts 48 mating to the holes 44. The marker plate 46, which is planar and parallel to the likewise planar mount plate 42, can be constructed of transparent plastic and have LEDs 38 disposed therein (as shown) or mounted on a surface thereof.

An alternate marker plate 50, shown in FIG. 4 only, may be shaped the same as marker plate 46 and have three posts 52 (only one visible) for securing it to the mount plate 42 by way of holes 44. Instead of using LEDs as fiducial markers, marker plate 50 has three markers 54 which may be radiopaque markers for angiography or CT scanning or which may be magnetic resonance markers for MR scanning. Only two of the markers 54 are visible in FIG. 4, but it will be appreciated that their placement and positioning would preferably be the same as shown for LEDs 38 in FIG. 3.

Considering now all of the FIGS., the operation of the invention for fractionated stereotactic radiotherapy will be discussed.

Prior to the patient undergoing either angiography, CT scanning, or MR scanning, the mold corresponding to tooth imprints 40 is made by placing mouth portion 39 with dental impression material against the teeth of the patient. Known techniques allow such a mold to be made in about 10 minutes. The mouth portion 39 would then be permanently fixed by adhesive or otherwise to the mount plate 42 (assuming mount plate 42 was not integral with mouth portion 39). The mount plate 42 may be about 3 cm by 6 cm and would have the three holes 44 therein.

A temporary adhesive may then be used to fix marker plate 50 to the mount plate 42 by having posts 52 inserted in the corresponding holes 44. The imaging system 24 images the brain of the patient and senses the position of the at least three markers 54. Three dimensional positions are determined within 0.2 mm throughout the region of interest. Although FIG. 1 has shown the imaging system 24 at the same location as the accelerator 12, it will be appreciated that they could be at separate locations. Instead of using the markers 54 sensed by imaging system 24, one could alternately use the LEDs 38 on the marker plate 46 during the initial imaging and the computer 32 could combine position data relative to the LEDs 38 with the imaging data from imager 24.

During the imaging, the head clamp ring 18 would not necessarily be used, but some patient restraint would normally be used just to remind the patient to hold still for the approximate 30 seconds for complete imaging.

After the diagnostic images have been obtained, a routine stereotactic radiosurgical planning session is conducted. After an acceptable plan has been arrived at the isocenter, or isocenters, of the plan are identified relative to the bite plate markers. This then creates a link between the external reference system, the markers, and the intracranial target.

The patient is then brought into the treatment area. They are positioned and immobilized through the use of comfortable head clamps. At this point the markers used in the diagnostic procedures can be localized through the use of a high precision digitizing probe (not shown).

Instead of using a digitizing probe (not shown) to locate specific marker points on the marker plate such as plate 50, the marker plate 50 could be separated from mount plate 42 and the marker plate 46 attached to mount plate 42 before mouth portion 39 is placed back in the patient with his or her teeth in registry with the imprints 40. Using marker plate 46, the infrared LEDs 38 are strobed and the camera system 34 identifies the exact position of the plate 46 with respect to six degrees of freedom. In other words, the use of at least three LEDs not in a line allows a precise determination of the position of plate 46 relative to x, y, and z axes and rotation about x, y, and z axes (hence six degrees of freedom).

Since the positions of the markers relative to the intracranial target (such as a brain tumor) are known, it will be known what the positions of the markers should be in order for the target to be at the isocenter of the accelerator 12. Camera system 34 provides the current position of the markers to the computer 32. comparing the current positions of the markers with the proper positions, the computer 32 computes the appropriate 3 dimensional translations and 3 axis rotations which are required to move the patient to the proper position. For each subsequent treatment after the first radiation treatment, the patient is again placed at the approximate treatment position, the positions of the fiducial markers are determined and the required movements are computed and performed.

Most importantly, the repositioning of the patient to the proper position for treatment does not use the bite plate 26. Instead such repositioning of the patient would use the head clamp ring 18 or other immobilizer device. Therefore, and since the bite plate 26 is not connected to the positioning structure, such repositioning does not put forces or torques on the bite plate 26. Thus, the position locator (bite plate) avoids the misalignments or errors which would otherwise to introduced by having a locator plate fixed to a structure used to reposition the patient.

In order to test the above system, both the known surface contour method as well as the present technique has been implemented in anatomical phantoms. To test out the accuracy and precision of the technique the phantom, a styrofoam manikin, was fitted with a rigid stereotactic frame. The phantom was then scanned and localized and placed into the correct treatment position. The anatomical contours and the bite plate markers were localized. The phantom then underwent a series of precise moves which included both individual translations and rotations and combined moves. These moves were carried out to within 0.1 mm and 0.2 degrees. After each move the contours and bite plate positions were again obtained. The inverse move, the move required to reposition the phantom back to isocenter was then computed. The results of the experiment showed that the contour method was able to reposition the phantom to within 2 mm of the initial position. The bite plate system was able to accomplish this move to within 0.1 mm.

The above increase in precision is nearly an order of magnitude. More importantly the dose gradient routinely obtained in radiotherapy results in a decrease in dose from the 90% intensity to the 50% intensity in approximately 2 mm. This means that tissues at the edge of the targeted volume have a high probability of receiving a subclinical dose for any given fraction. The increased accuracy obtainable with the bite plate system substantially reduces the probability of positional targeting errors.

Although the locator is a bite plate in the preferred embodiment, the present invention broadly contemplates other locators which can be place in registry with a portion of a patient.

Advantageously, the bite plate used herein is a non-invasive locator and avoids the discomfort associated with techniques requiring one to put one or more holes in a patient or otherwise remove tissue from a patient. However, the present invention also has applicability to invasive locators which are mechanically independent of any patient positioning structure (i.e., members used to change or adjust patient position).

Although the present description has assumed the use of three markers such as LEDs 38 or markers 54, more than three could be used and may help provide more accurate positioning information. For example, a fourth LED in or out of the plane defined by LEDs 38 could provide useful additional information.

Various computer programs may be used to provide the relationship between intracranial or other target points and the markers or LEDs. Likewise, various computer programs may be used to compute the appropriate 3 dimensional translations and 3 axis rotations which are required to move the patient to the proper position.

The discussion has so far assumed that one would want to adjust the patient position after re-attachment of the bite plate so that the patient position for a second medical procedure (either diagnostic or remedial) is identical to the initial patient position. However, the present invention also contemplates that the second position could be stabilized offset from the first patient position. In that case, the second medical procedure could use a transformation so that treatment by the probe 20 or imaging by imager 24 could be adjusted to take into account differences between the first patient position and the second patient position. Because the accelerator 12 movement relative to the patient is normally limited to arcs about two transverse axes, it would be more difficult to adjust for offset between the first patient position and the second patient position, although a radiation head with a greater degree of freedom of movement could allow one to use such a transformation. Using such a transformation technique would allow one to secure the patient position without requiring that the patient position is identical to what it was for the previous treatment. Under such circumstances, a positioner which simply stabilizes the patient position would be sufficient even if the positioner did not provide the ability to move or re-position the patient by way of it. Moreover, if the medical procedure was sufficiently fast, one might be able to avoid use of even a simply position-stabilizing positioner.

Although not shown, one could also have a set of LEDs on the radiation emitting head, collimator, or other part of the linear accelerator 12 and/or the head support. By proper placement of the LEDs to detect any misalignments of the type discussed in the inventors' incorporated by reference patents, the various misalignment correcting mechanisms of those patents would not be required. Instead of correcting for misalignments using those mechanisms, use of such LEDs on part of the linear accelerator 12 and/or the head support would allow the system to not only compute the translation/rotation of the patient relative to the nominal isocenter of the linear accelerator, but would allow the system to compute the actual isocenter. Thus, the patient could be moved to proper position relative to the actual isocenter. This compensates for any offset between the nominal isocenter (isocenter absent the misalignments) and the actual isocenter.

Figure 5:
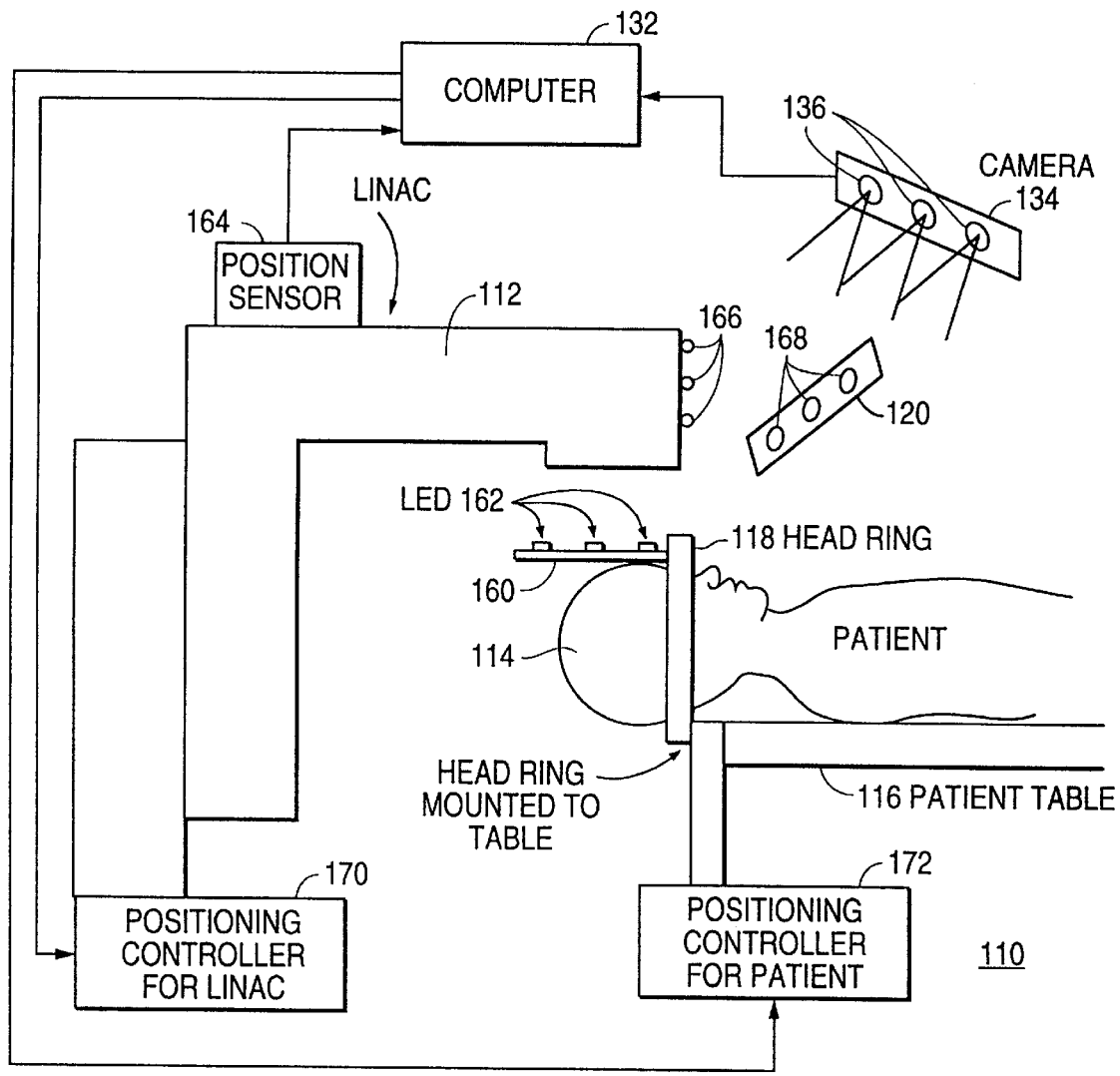
FIG. 5 is a simplified side view of a second embodiment system of the present invention.

Turning now to FIG. 5, an alternate embodiment of the present invention is shown. The alternate embodiment 110 has components in the 100 series with the same last two digits as the corresponding component, in any, of the embodiment 10 of FIG. 1 and the parts of FIGS. 2–4. Thus, linear accelerator 112, table 116, head ring 118, probe 120, computer 132, camera system 134, and cameras 136 are constructed and operate as discussed above except for any differences detailed hereafter. Patient's head 114 is positioned like the patient's head 14 of FIG. 1. For ease of illustration components similar to components 22, 24, 28, and 30 in FIG. 1 are not shown in FIG. 5, but such components would be used in system 110 and would be constructed, connected, and operable as discussed above.

No bite plate is used in the second embodiment 110. The head ring 118 of FIG. 5 is different from head ring 18 of FIG. 1 in that it has LEDs on this head support, which feature was mentioned above, but not previously shown. The head ring 118 specifically has a plate 160 with LEDs 162 mounted thereon. In the arrangement of FIG. 5, the head ring 118 serves as the immobilizer and positioner for the patient as ring 18 does in FIG. 1. However, ring 118 additionally serves as the localizer in that the LEDs 162 function like LEDs 38 (FIGS. 2–4) of the system 10 of FIG. 1. That is, the LEDs 162 would be controlled by wires and a drive circuit (not shown in FIG. 5) such as the wires 28 and circuit 30 previously discussed relative to FIG. 1. The LEDs 162 are imaged by cameras 136 so that the relative position of the patient and the medical devices such as accelerator 112 can be determined and, if necessary, adjusted by moving the patient and/or the medical devices or portions thereof.

The mounting of the LEDs to the head support or ring 118 via plate 160 does not realize some of the advantages discussed above relative to separating the functions of immobilization (i.e., securing patient in position) and localization (i.e., sensing accurately the position of the patient or a part of the patient). (As mentioned above, an important advantage of separating these functions in the first embodiment is that forces or moments or torque are not placed on the patient-localizer interface by using the localizer for immobilization and/or positioning purposes.) However, it may provide sufficient precision for some applications, especially where a single medical treatment (i.e., as opposed to multiple treatments requiring repeat fixation) is to be performed. It avoids the necessity of using a localizer separate from the immobilizer. Under certain circumstances, this may be simpler, faster, and/or otherwise preferable to the first embodiment.

The arrangement of FIG. 5 may optionally include either or both of a standard position sensor 164 for a linear accelerator and three or more LEDs 166 mounted to the accelerator 112. Sensor 164 may supply accelerator position information directly to the computer 132 in known fashion, whereas LEDs 166 would be strobed sequentially by a circuit similar to 30 of FIG. 1 and the accelerator position is supplied to the computer by sensing from the camera system 134 as discussed for the other LEDs. Although the position sensor 164 and LEDs 166 are shown mounted to a given portion of the accelerator, they may be mounted to other portions and/or other associated mechanical parts not illustrated herein, but shown in the two incorporated by reference issued patents, such as a collimator.

The probe 120 may have three or more LEDs 168 thereon for being strobed (drive circuit not shown) and allowing camera system 134 to supply information about the probe position to computer 132. As with LEDs 166 and other sets of LEDs discussed herein for localizing a given component (or patient with component attached thereto), LEDs 168 include at least three LEDs which are not in a straight line and which therefore uniquely define a plane.

Computer 132 is preferably attached to an accelerator positioning controller 170 and a patient positioning controller 172. Accelerator positioning controller 170 may be used to adjust the position of the accelerator 112 (or portions thereof or associated mechanical parts not illustrated herein, but shown in the two above incorporated by reference issued patents, such as a collimator). Patient positioning controller 172 may be used to adjust the position of the patient (or portions thereof such as head).

Figure 6:
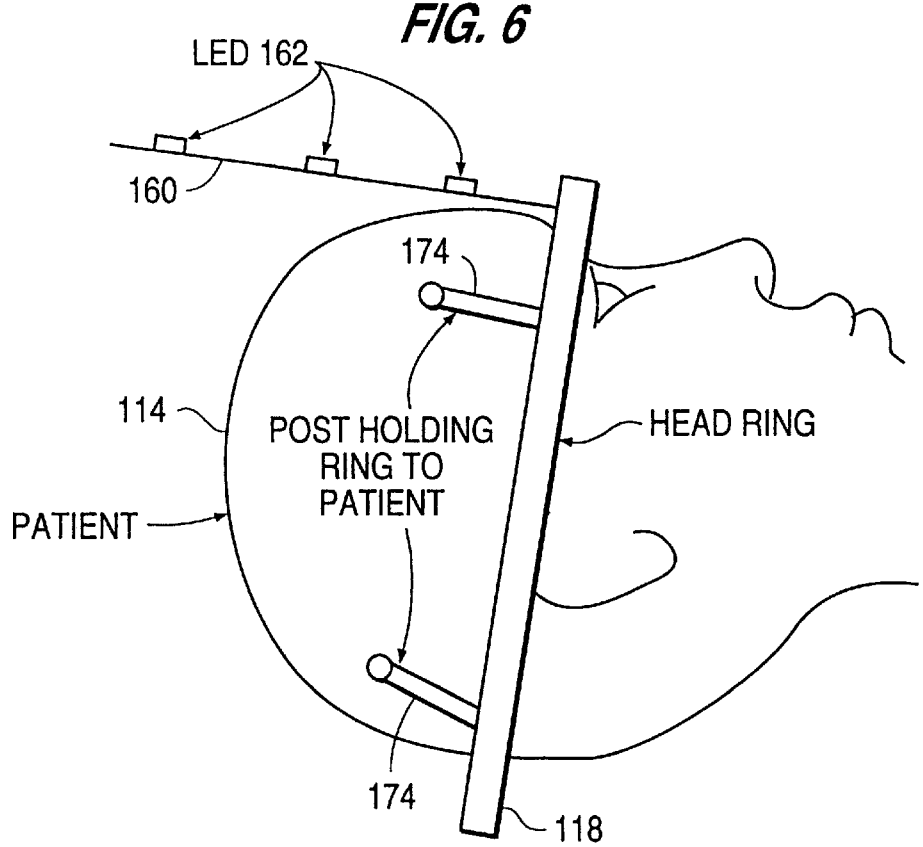
FIG. 6 is an enlarged and more detailed side view of a portion of the system of FIG. 5.
Figure 7:
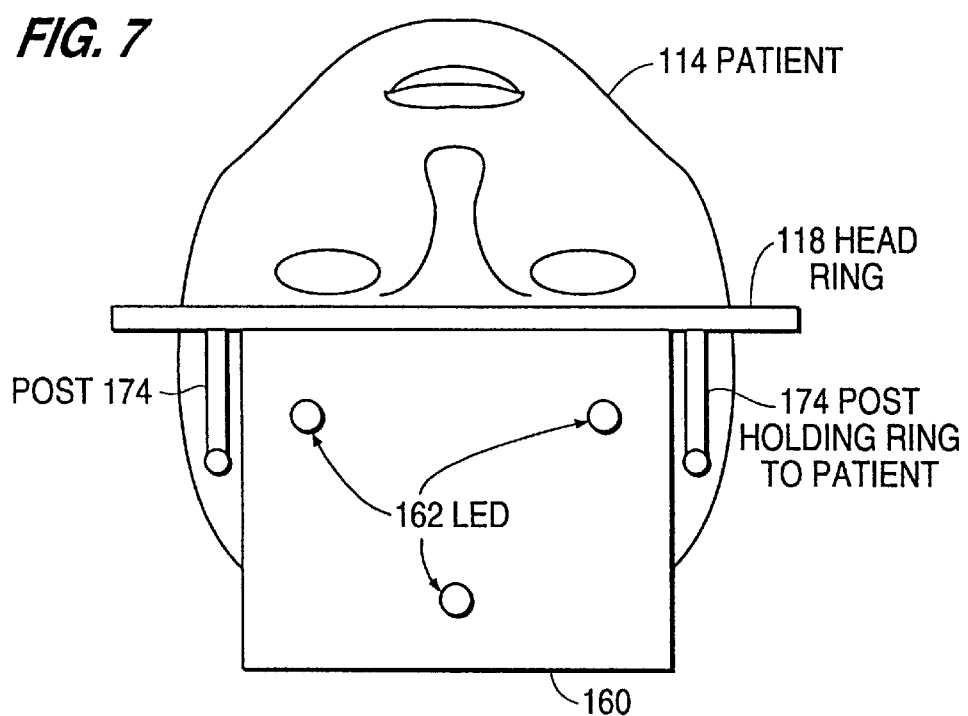
FIG. 7 is a top view of a portion of the system of FIG. 5 and corresponding to FIG. 6.

With reference now to FIGS. 6 and 7, more details of head ring 118 and associated components are shown. The ring 118 has two posts 174 on each side of the patient's head 114, which posts may be anchored or fixed to the patient's skull after use of an anesthetic. The mounting of the ring 118 via posts 174 is done in known fashion.

The ring 118 has standard hardware fittings (not shown) such as commonly used for attaching such parts as CT (computerized tomography) brackets or angiography brackets (not shown). However, instead of using those fittings for CT or angiography brackets, plate 160 is secured to ring 118 by such fittings with alignment posts (not shown) to insure proper relative positioning of plate 160 and ring 118.

Figure 8:
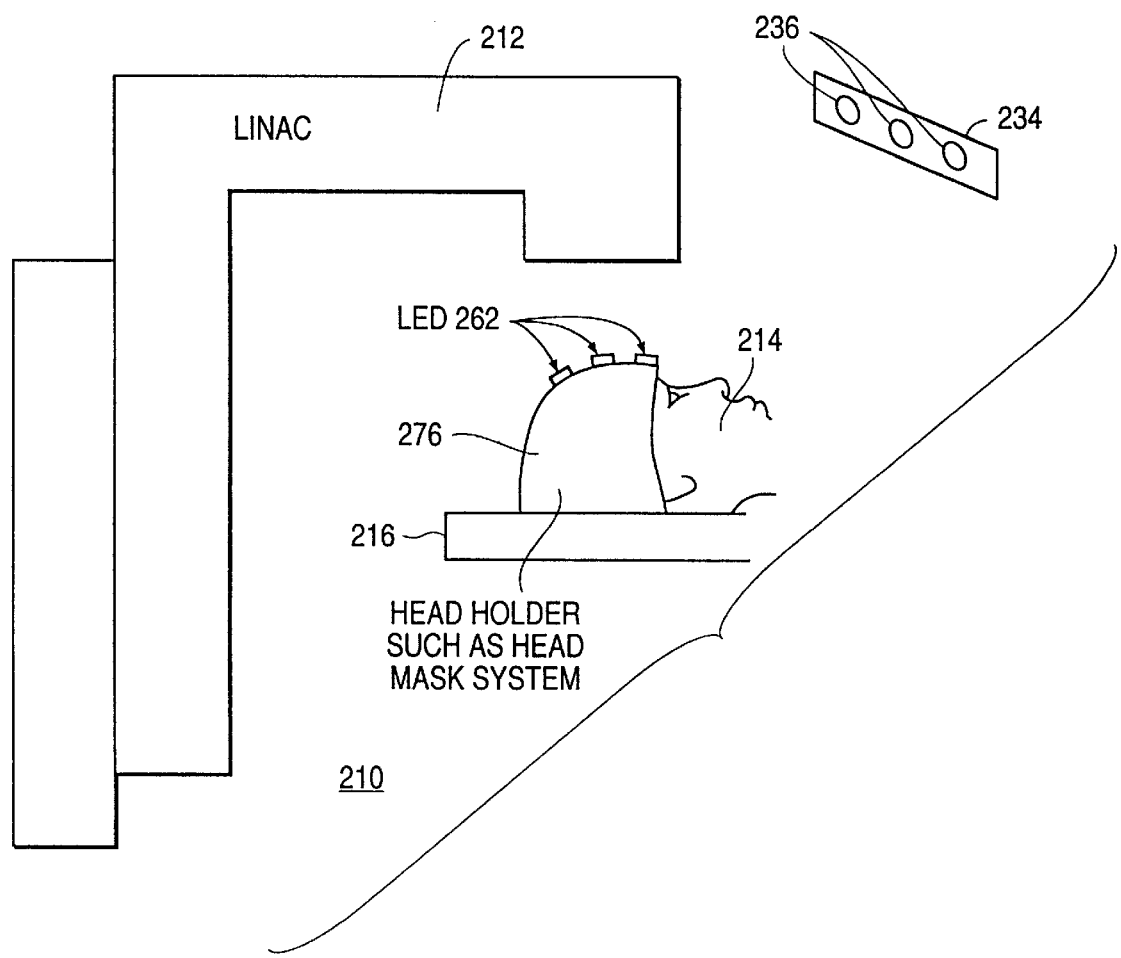
FIG. 8 is a simplified side view of a third embodiment system of the present invention.

With reference now to FIG. 8, a third embodiment system 210 is shown as having a head holder 276 such as a head mask system, instead of the head ring. The embodiment 210 has components in the 200 series with the same last two digits as the corresponding component, in any, of the embodiment 110 of FIGS. 5–7. Thus, linear accelerator 212, table 216, camera system 134, and cameras 136 are constructed and operate as discussed above. Patient's head 214 is positioned like the patient's head 114 of FIGS. 5–7, but is secured by holder 276 having LEDs 262 thereon. The system 210 has no head ring. Other than that, the system 210 would have various other components shown and/or discussed relative to FIGS. 5–7 and which are not shown for ease of illustration. It would operate as discussed for the system 110.

Figure 9:
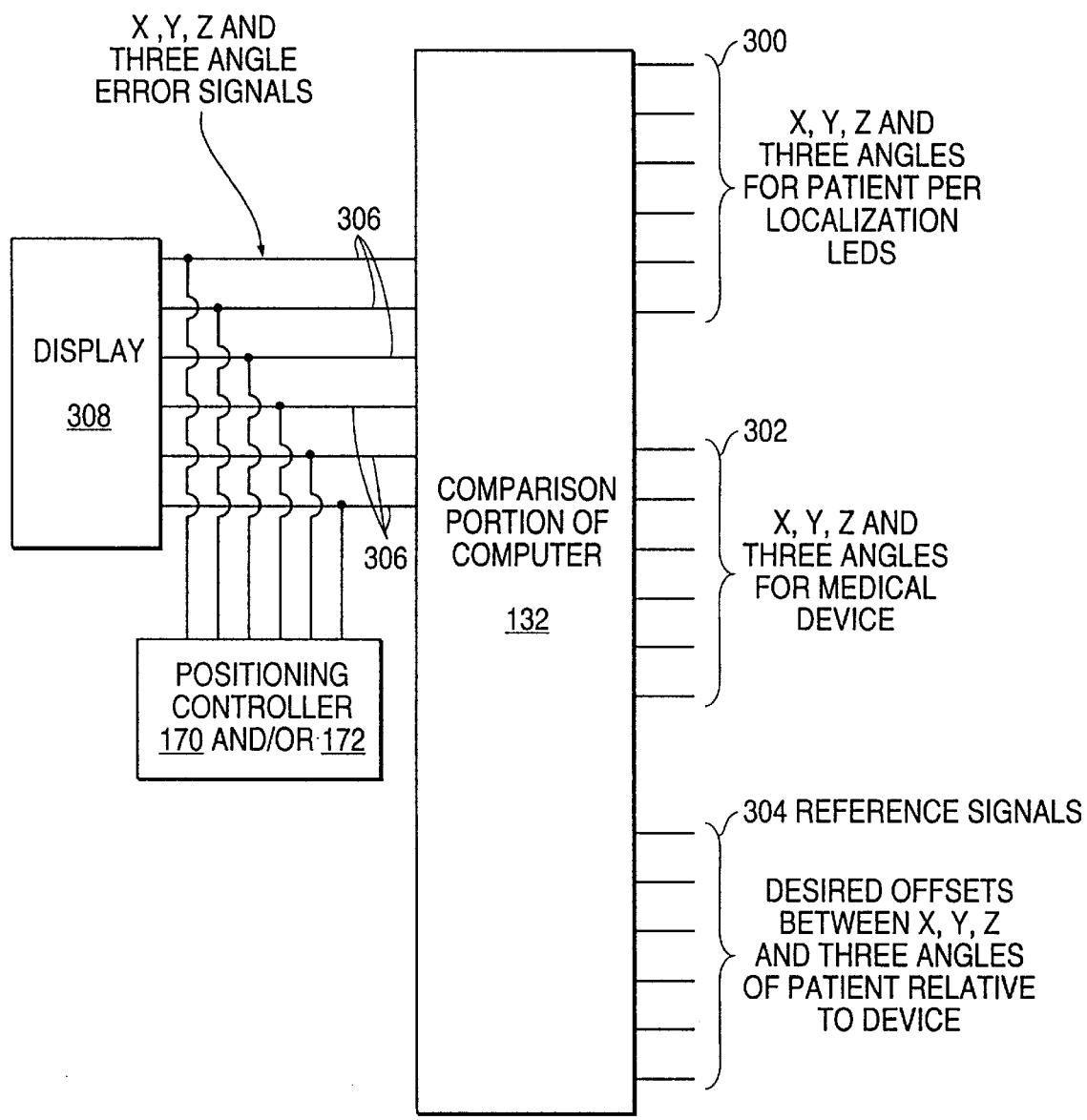
FIG. 9 is a schematic illustrating a comparison technique used with the invention.

Turning now to FIG. 9, more details of a control arrangement usable with computer 132 (as well as the similar computer used with system 210 of FIG. 8) are shown. In particular, a comparison portion or operation of the computer 132 receives six signals 300 corresponding to position and orientation defining information (x,y,z position and angular information for first, second, and third angles) of the patient by operation of the patient localization LEDs (such as 38, 162, or 262 of the different embodiments). The signals 300 may be determined from sequentially strobing the patient localization LEDs, sensing the light by camera systems 34, 134, or 234, and processing the data in the computer.

The comparison portion of the computer (this may simply be a program within the computer) also receives six signals 302 corresponding to position and orientation defining information (x,y,z position and angular information for first, second, and third angles) of a medical device such as linear accelerator (as by way of position sensor 164 and/or LEDs 166 of FIG. 5) or the probe 120 of FIG. 5 (by way of LEDs 168 of FIG. 5). Six reference signals corresponding to position and orientation offsets defining information (x,y,z position and angular information for first, second, and third angles) representing desired offsets between the patient's position and orientation and the medical device's position and orientation are also supplied to the comparison portion of the computer.

The comparison portion or program of the computer takes the differences between the x,y,z position and angular information for first, second, and third angles of the patient received on lines 300 and the corresponding x,y,z position and angular information for first, second, and third angles of the medical device received on lines 302. This provides six signals representing the actual offsets, which signals are then compared with the desired offsets supplied by lines 304 to generate six error signals on lines 306 supplied to display 308.

The display 308, which may have separate displays for each of the six error signals, allows an operator to manually observe a difference between the desired offset and the actual offset. The operator may, for example, read display 308 as showing an error of 2 mm in the y direction and 3 degrees relative to a second angle (i.e., one of the three angles defining orientation of an object). The operator may then manually adjust, either directly or by way of a powered device (not shown), the patient and/or the medical device relative to both the y direction and the second angle until the corresponding error signals are zero or otherwise minimized such as made essentially zero. In that fashion, the proper positioning of the patient is obtained before the radiation therapy is actually started.

Instead of using display 308 to allow manual adjustment for nulling or minimizing the six error signals 306, an automatic feedback control can be used for that purpose. In that case, the six error signals are supplied to a positioning controller 170 or 172. The positioning controllers 170 and 172 respectively control the position and orientation of the linear accelerator and the patient. By using either or both positioning controllers as part of a feedback control, the six error signals can automatically be nulled or minimized to bring the patient and medical device into proper relative positions and orientations prior to beginning a medical procedure such as radiosurgery.

Figure 10:
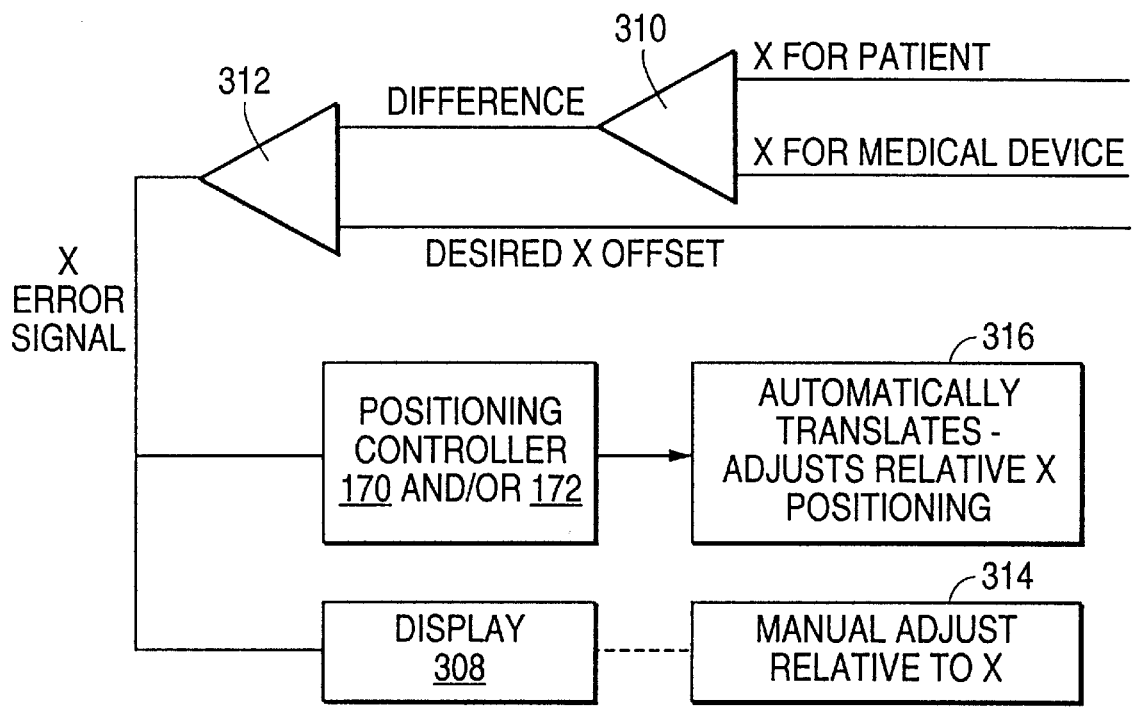
FIG. 10 is a schematic illustrating a comparison technique for one of the six variables corresponding to six degrees of freedom which are used in FIG. 9.

Turning to FIG. 10, the feedback control principles of the present invention are illustrated relative to the x direction, it being understood that similar feedback arrangements would be used also for y and z directions and for the three angles. The patient x signal and the medical device x signal are supplied to a differential amplifier 310 supplying an actual x difference signal at its output. The actual x difference signal is supplied to differential amplifier 312, whose other input is the reference signal corresponding to the desired x offset. The output of amplifier 312 is an x error signal. Although differential amplifiers 310 and 312 are shown as circuit components for illustration of the principles of operation, it will be readily appreciated that the comparisons corresponding to each of these amplifiers may be performed digitally by a computer program comparing the various signals.

The x error signal is supplied to the display 308 such that an operator may manually adjust the x offset as indicated schematically at block 314. Alternately or additionally, the x error signal is supplied to positioning controller 170 and/or 172 and would be used by the positioning controller to automatically adjust (as indicated by block 316) the relative x offset between the patient and the medical device to reach the desired x offset.

Figure 12:
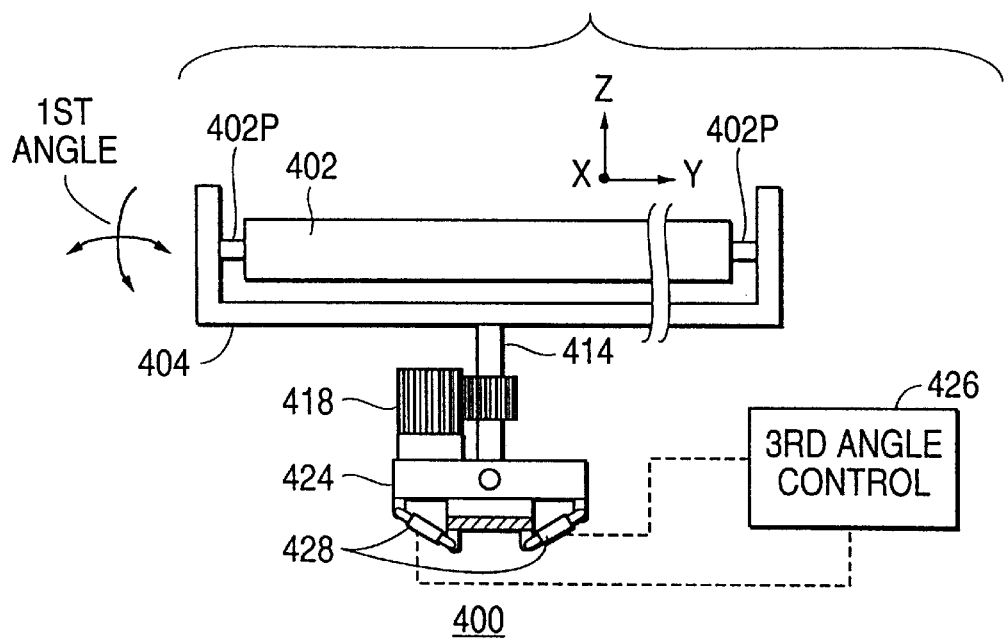
FIG. 12 is a simplified side view with some parts broken away of portions of the positioning controller of FIG. 11.
Figure 11:
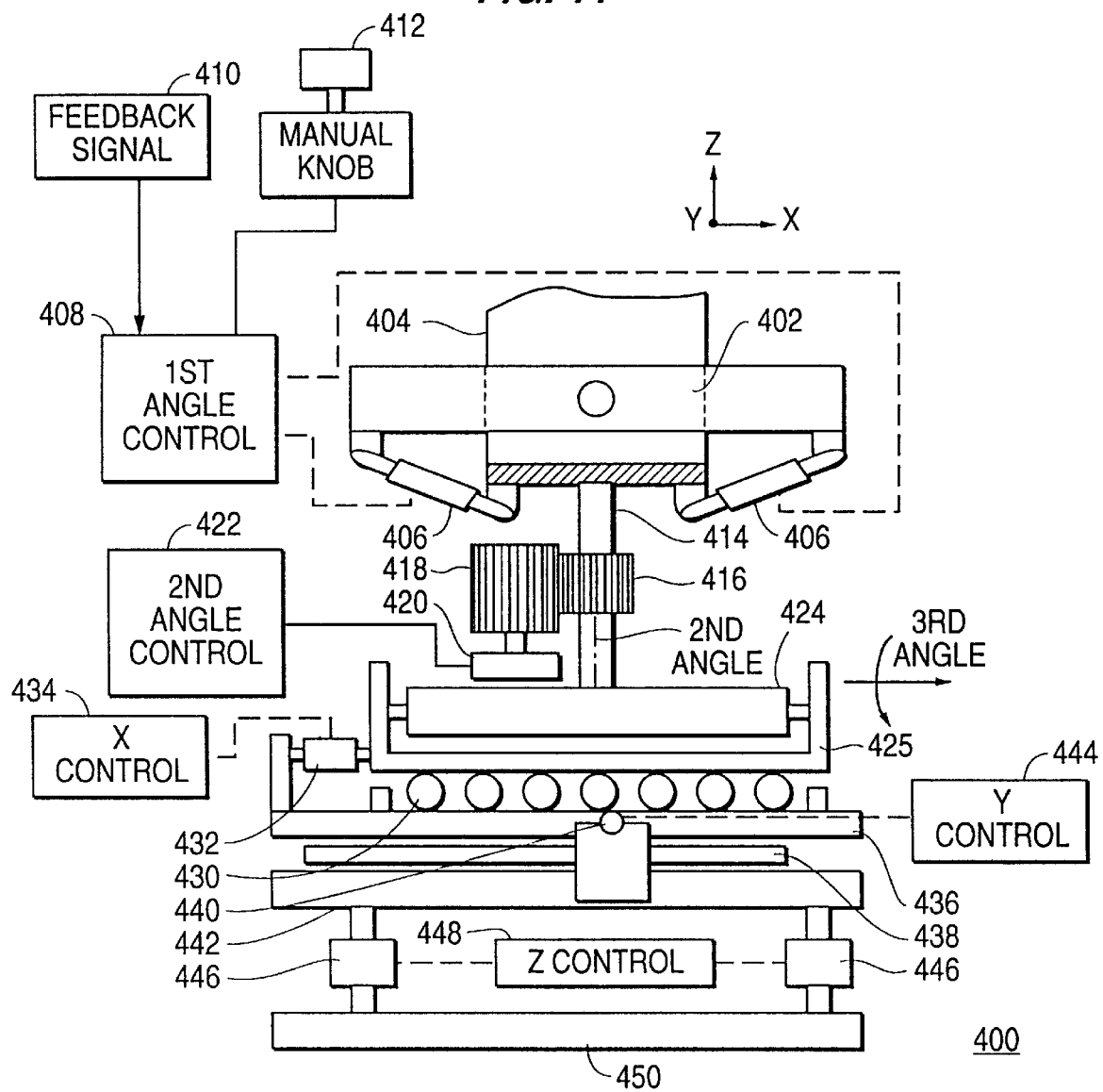
FIG. 11 is a simplified front view with some parts broken away of a positioning controller.

FIGS. 11 and 12 show front and side views, with parts broken away and some parts shown only in one of the views, of a positioning controller 400 of a type which might be used for the positioning controller 170 and/or positioning controller 172. This position controller is illustrative in that it shows ability to control the ability to control translations in three directions x,y,z and to control the three angles corresponding to orientation. In actual practice, some of the six degrees (x,y,z translations and three angles) of relative positioning between the patient and the medical device would be adjusted by adjusting the patient position and other of the degrees of freedom would be adjusted by moving the medical device. Thus, a given positioning controller would not necessarily require the ability to adjust relative to all six degrees of freedom. Further, the mechanisms of these FIGS. are illustrative and various other mechanical arrangements for realizing the three translations (x,y,z) and the three angular adjustments could be used.

An example may help explain why each of the positioning controllers 170 and 172 of FIG. 5 need not adjust for all six degrees of freedom. With reference momentarily back to FIG. 1, if the patient is offset from the desired angle of offset corresponding to accelerator axis 12X, one may simply adjust the accelerator position. Suppose the patient is offset by 3 degrees relative to his or her desired position and the arc (accelerator rotation about 12X) to be used for radiation treatment is between 70 and 80 degrees. Instead of rotating the patient three degrees about axis 12X before applying the radiation, one may simply perform the radiation treatment with the accelerator moving over an arc between 73 and 83 degrees (or between 67 and 77 degrees depending on the direction of the 3 degree offset from desired position).

The positioning controller 400 of FIGS. 11 and 12 has a platform 402. If controller 400 is used as patient controller 172 of FIG. 5, the platform 402 may simply be the patient table 116 of FIG. 5. If controller 400 is used as LINAC or linear accelerator controller 170 of FIG. 5, the platform 402 may simply be a platform supporting the accelerator. In either case, platform 402 rotates about the first angle (FIG. 12) by opposite end pivot connections 402P relative to its support 404 and under control of hydraulic actuators or cylinders 406 (FIG. 11 only). The cylinders 406 operate under control of a first angle control 408 based on a feedback signal 410 (in the automatic feedback setup) or a control signal from manual knob 412 (in the manual control setup or mode).

Adjustments relative to the second angle (FIG. 11) are made by shaft 414 rotating about a vertical axis by gear 416 rotating from gear 418 which in turn is driven by motor 420. The motor 420 is controlled by second angle control circuit 422 (it may also be a computer controlled function instead of a circuit). Second angle control 422, like the angle and x,y,z controls discussed below, would have inputs (feedback signals or manual controls) similar to parts 410 and/or 412, but these are not shown for ease of illustration.

Shaft 414 is seated in plate 424 rotatably connected at opposite ends to member 425 to allow rotation relative to the third angle (FIG. 11) by third angle control 426 controlling hydraulic cylinders 428.

Member 425 may slide in the x direction by moving on roller bearings 430 by operation of hydraulic cylinder 432 controlled by x control 434. The roller bearings 430 are on member 436 which in turn moves in the y direction (perpendicular to the FIG. 11 plane of view) by sliding on roller bearings 438 (only one visible) from hydraulic cylinder 440 having one end secured to member 436 and the other end secured to member 442. Cylinder 440 operates under control of y control 444. Member 442 may translate in the z direction by hydraulic cylinders 446 lifting and lowering it under control of z control 448. The lower ends of the cylinders 446 are attached to base 450.

Therefore, the controller 400 allows adjustment relative to all six degrees of freedom. Various alternative arrangements could of course be used.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A medical method comprising the steps, not necessarily in order, of:

attaching a mechanically free locator to the patient, the locator having at least 3 fiducial markers thereon and being in registry with a portion of the patient;

using the fiducial markers a first time to get precise positioning information relative to at least part of the patient;

performing a first medical procedure on the patient;

after the first medical procedure, removing the locator from the patient;

at a later time after the removing of the locator, re-attaching the locator to the patient, the locator again being in registry with the portion of the patient and having an identical orientation relative to the portion of the patient as when the locator was previously attached;

after the re-attaching step, using the fiducial markers a second time to get precise positioning information relative to the at least part of the patient;

after the re-attaching step, performing a second medical procedure on the patient; and wherein before performing the second medical procedure, the patient is positioned using a positioner independent of the locator to adjust and secure at least the portion of the patient in a desired position.

2. The medical method of claim 1 wherein the attaching and re-attaching of the locator is non-invasive.

3. The medical method of claim 1, wherein the using of the fiducial markers the first and second times utilizes a sensing subsystem for sensing the positions of the fiducial markers.

4. A system for medical procedures, the system comprising:

a locator attachable to a patient, having at least 3 LEDs thereon, and having a registration portion for registration with a portion of a patient's body, the registration portion allowing removal of the locator from the patient and re-attachment to the patient with an identical orientation relative to the portion of the patient as when the locator was previously attached, the locator being mechanically free such that a patient is positionable without applying forces to the locator during patient positioning; a positioner independent of the locator and operable to adjust and to secure at least the portion of the patient in a desired position; and a sensing subsystem for sensing the positions of the LEDs when the patient is in the desired position.

5. The system of claim 4 wherein the locator is non-invasive.

6. The system of claim 4 further comprising an imaging subsystem for imaging the patient.

7. A medical method comprising the steps, not necessarily in order, of:

positioning a patient for a first medical procedure;

attaching a locator to a patient, the locator having at least 3 fiducial markers thereon and being in registry with a portion of the patient, the locator being mechanically free such that a patient is positionable without applying forces to the locator during patient positioning;

using fiducial markers a first time to get precise positioning information relative to at least part of the patient;

performing a first medical procedure on the patient;

after the first medical procedure, removing the locator from the patient;

at a later time after the removing, reattaching the locator to the patient, the locator again being in registry with the portion of the patient and having an identical orientation relative to the portion of the patient as when the locator was previously attached;

after the re-attaching step, using fiducial markers a second time to get precise positioning information relative to the at least part of the patient; and after the re-attaching step, performing a second medical procedure on the patient; and wherein the locator is a bite plate with an external portion connected thereto, and the fiducial markers are on the external portion, and wherein the attaching includes using a mold of dental impression material to bring the bite plate in registry with teeth of the patient, and wherein the re-attaching uses the mold to bring the bite plate in registry with teeth of the patient with an identical orientation relative to the teeth as when the bite plate was previously attached; and wherein the second medical procedure is a remedial procedure treating at least one problem precisely localized in the first medical procedure; and wherein, before performing the second medical procedure, the patient is positioned using a positioner independent of the locator to adjust patient position and to secure at least the portion of the patient in a desired position.

8. The medical method of claim 7 wherein the first medical procedure is an imaging of at least a portion of the patient.

9. The medical method of claim 7 wherein the second medical procedure includes radiotherapy.

10. The medical method of claim 7 wherein both the first and second medical procedures include radiotherapy.

11. A system for medical procedures, the system comprising:

a locator attachable to a patient, having at least 3 fiducial markers thereon, and having a registration portion for registration with a portion of a patient's body, the registration portion allowing removal of the locator from the patient and re-attachment to the patient with an identical orientation relative to the portion of the patient as when the locator was previously attached, the locator being mechanically free such that a patient is positionable without applying forces to the locator during patient positioning;

a positioner independent of the locator and operable to adjust and to secure at least the portion of the patient in a desired position; and wherein the locator is a bite plate with an external portion connected thereto, and the fiducial markers are on the external portion, and the bite plate has a mold to bring the bite plate in registry with teeth of the patient with an identical orientation relative to the teeth as when the bite plate was previously attached.

12. The system of claim 11 further comprising a radiotherapy apparatus for applying radiation treatment to a patient, the positioner and sensing subsystem allowing proper positioning of the patient for applying radiation treatment.

13. A system for medical procedures, the system comprising:

a locator attachable to a patient, having at least 3 fiducial markers thereon;

a medical device means for performing a diagnostic imaging or a therapeutic medical procedure on a patient;

a sensing subsystem for sensing the positions of the fiducial markers when the patient is in a position for performing the medical procedure using the medical device;

a first comparison means for comparing positioning information of the fiducial markers to positioning information indicative of a position of the medical devices, and for supplying information indicative of an actual offset between the position of the fiducial markers and the position of the medical device; and a second comparison means for comparing the actual offset information with desired offset information and for generating an error signal based thereon.

14. The system of claim 13 wherein the locator has a registration portion for registration with a portion of a patient's body, the registration portion allowing removal of the locator from the patient and re-attachment to the patient with an identical orientation relative to the portion of the patient as when the locator was previously attached, the locator being mechanically free such that a patient is positionable without applying forces to the locator during patient positioning; and wherein the locator is a bite plate with an external portion connected thereto, and the fiducial markers are on the external portion, and the bite plate has a mold to bring the bite plate in registry with teeth of the patient, and the mold is operable to bring the bite plate in registry with teeth of the patient with an identical orientation relative to the teeth as when the bite plate was previously attached.

15. The system of claim 13 wherein the locator is selected from the group consisting of: a head ring secured to a support and a head holder secured to a support.

16. The system of claim 13 wherein the locator is a head ring and has a member secured thereto, and wherein the three fiducial markers are mounted to the member so as to uniquely define a plane.

17. A method for performing a diagnostic imaging or a therapeutic medical procedure comprising the steps of, not necessarily in order:

attaching a mechanically free locator to a patient, the locator having at least 3 fiducial markers thereon;

placing the patient adjacent a medical device operable for performing said diagnostic imaging or therapeutic medical procedure on a patient;

sensing the positions of the fiducial markers when the patient is in a position for performing the diagnostic imaging or therapeutic medical procedure using the medical device; and generating error signals indicating differences between actual patient position information relative to the medical device and a desired patient position relative to the medical device.

18. The method of claim 17 further including the step of adjusting the relative positioning of the patient and the medical device to null or minimize the error signals.

19. The method of claim 17, further including the step of:

performing a first medical procedure on the patient.

20. The method of claim 19, further including the steps of:

removing the locator from the patient after performing said first medical procedure;

later reattaching the locator to the patient at an identical position and orientation relative to the patient;

again sensing the fiducial markers and generating error signals dependent on differences between actual patient position information relative to the medical device and a desired patient position relative to the medical device; and performing a second medical procedure on the patient.

* * * * *

UNITED STATES PATENT AND TRADEMARK OFFICE
CERTIFICATE OF CORRECTION

PATENT NO : 5,954,647
DATED : September 21, 1999
INVENTOR(S) : Frank J. BOVA, et al.

It is certified that error appears in the above-identified patent and that said Letters Patent is hereby corrected as shown below:

Claim 13, line 52, delete "devices," and insert therefor --device,--.

Signed and Sealed this

Sixth Day of February, 2001

Attest:

Q. TODD DICKINSON

Attesting Officer

Director of Patents and Trademarks